(12) United States Patent
Besidski et al.

(10) Patent No.: US 9,718,805 B2
(45) Date of Patent: Aug. 1, 2017

(54) TRIAZOLE COMPOUNDS AND THEIR USE AS GAMMA SECRETASE MODULATORS

(71) Applicant: Acturum Life Science AB, Sodertalje (SE)

(72) Inventors: Yevgeni Besidski, Tumba (SE); Ulrika Yngve, Uppsala (SE); Kim Paulsen, Huddinge (SE); Christian Erik Linde, Stockholm (SE); Jonas Malmborg, Linkoping (SE)

(73) Assignee: Acturum Life Science AB, Sodertalje (SE)

( * ) Notice: Subject to any disclaimer, the term of this patent is extended or adjusted under 35 U.S.C. 154(b) by 0 days.

(21) Appl. No.: 14/895,519

(22) PCT Filed: Jun. 3, 2014

(86) PCT No.: PCT/EP2014/061501
§ 371 (c)(1),
(2) Date: Dec. 3, 2015

(87) PCT Pub. No.: WO2014/195322
PCT Pub. Date: Dec. 11, 2014

(65) Prior Publication Data
US 2016/0108022 A1    Apr. 21, 2016

(30) Foreign Application Priority Data
Jun. 4, 2013   (SE) ..................... 1350684

(51) Int. Cl.
*C07D 403/12* (2006.01)
*A61K 31/4196* (2006.01)
*A61K 45/06* (2006.01)

(52) U.S. Cl.
CPC ........ *C07D 403/12* (2013.01); *A61K 31/4196* (2013.01); *A61K 45/06* (2013.01)

(58) Field of Classification Search
None
See application file for complete search history.

(56) References Cited

U.S. PATENT DOCUMENTS

2012/0295891 A1* 11/2012 Van Brandt .......... C07D 401/12
514/218

FOREIGN PATENT DOCUMENTS

| | | |
|---|---|---|
| WO | WO 2004/073705 | 9/2004 |
| WO | WO 2005/013985 | 2/2005 |
| WO | WO 2005/054193 | 6/2005 |
| WO | WO 2005/115990 | 12/2005 |
| WO | WO 2007/125364 | 11/2007 |
| WO | WO 2007/135969 | 11/2007 |
| WO | WO 2007/139149 | 12/2007 |
| WO | WO 2008/097538 | 8/2008 |
| WO | WO 2008/099210 | 8/2008 |
| WO | WO 2008/100412 | 8/2008 |
| WO | WO 2008/156580 | 12/2008 |
| WO | WO 2009/020580 | 2/2009 |
| WO | WO 2009/032277 | 3/2009 |
| WO | WO 2009/087127 | 7/2009 |
| WO | WO 2009/103652 | 8/2009 |
| WO | WO 2010/052199 | 5/2010 |
| WO | WO 2010/053438 | 5/2010 |
| WO | WO 2010/083141 | 7/2010 |
| WO | WO 2010/132015 | 11/2010 |
| WO | WO 2011/006903 | 1/2011 |
| WO | WO 2011/014535 | 2/2011 |
| WO | WO 2011/086098 | 7/2011 |
| WO | WO 2011/086099 | 7/2011 |
| WO | WO 2011/092272 | 8/2011 |
| WO | WO 2012/009309 | 1/2012 |

OTHER PUBLICATIONS

Antonio R. Damasio, Alzheimer's Disease and Related Dementias, Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL: http://www.cnn.com/2003/HEALTH/conditions/09/24/alzheimers.drug.ap/indez.html, pp. 1 and 2.*
Beher D, Curr "Secrease Modulation and it's Promise for Alzheimer's Disease: a Rationale for Drug Discovery" *Top Med Chem;* 8(1):34-7; 2008.
Weggen et al. "A Subset of NSAIDs Lower Amyloidogenic Aβ42 Independently of Cyclooxygenase Activity" Nature 414(6860), 212-216 (2003).
Kounnas et al. "*Modulation of Secretase Reduces B-Amyloid Deposition in a Transgenic Mouse Model of Alzheimer's Disease*" Neuron 67, 769-780 (2010).
Zettl et al. "*Exploring the Chemical Space of γ-Secretase Modulators*" Trends Pharmacol. Sci. 31, 402-410 (2010).
Jarowicki, K.; et al. "Protecting Groups". Perkin Trans.1, issue 18, p. 2109, 2001.

* cited by examiner

*Primary Examiner* — Alicia L Otton
(74) *Attorney, Agent, or Firm* — Baker & Hostetler LLP

(57) ABSTRACT

The present invention relates to compounds of formula (I) and pharmaceutically acceptable salts thereof. The invention also relates to pharmaceutical compositions comprising these compounds, to processes for making these compounds, and to their use as medicaments for treatment and/or prevention of Aβ-related diseases.

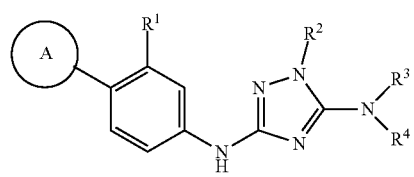

18 Claims, No Drawings

TRIAZOLE COMPOUNDS AND THEIR USE AS GAMMA SECRETASE MODULATORS

CROSS-REFERENCE TO RELATED APPLICATIONS

This application is the National Stage of International Application No. PCT/EP2014/061501, filed Jun. 3, 2014, which claims the benefit of SE application number 1350684-5, filed Jun. 4, 2013, the disclosures of which are incorporated herein by reference in their entireties.

The present invention relates to aminotriazole compounds and pharmaceutically acceptable salts thereof. The present invention also relates to pharmaceutical compositions comprising these compounds, to processes for making these compounds, and to their use as medicaments for treatment and/or prevention of various Aβ-related diseases.

BACKGROUND

The prime neuropathological event distinguishing Alzheimer's disease (AD) is deposition of the amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Aβ can be found in both plasma, cerebrospinal fluid (CSF), and in the medium from cultured cells, and is generated as a result of APP proteolysis. There are two main cleavages of APP that results in Aβ production, the so-called β-, and γ-cleavages. The β-cleavage, which generates the N terminus of Aβ, is catalyzed by the transmembrane aspartyl protease BACE1. The γ-cleavage, generating the Aβ C termini and subsequent release of the peptide, is affected by a multi-subunit aspartyl protease named γ-secretase. Both BACE1 and γ-secretase process APP at different sites, resulting in Aβ peptides of different lengths and heterologous N- and C-termini. The invention described herein covers all N-terminal variants of Aβ. Therefore, for the sake of simplicity, all N-terminal variants will be covered by the denotation Aβ.

The activity of γ-secretase causes the liberation of many Aβ peptides, such as Aβ37, Aβ38, Aβ39, Aβ40, Aβ42 and Aβ43, of which Aβ40 is the most common. These peptides show a different propensity to aggregate, and in particular Aβ42 is prone to form oligomers and fibrillar deposits. Intriguingly, human genetics strongly support a key role for Aβ42 as a key mediator of Alzheimer pathogenesis. Indeed, more than 150 different mutations causing familial Alzheimer's disease either result in an increase in the ratio of Aβ 42/40 peptides produced or affect the intrinsic aggregation behaviour of Aβ. Based on this knowledge, Aβ42 has become a prime target for therapeutic intervention in AD (Beher D, *Curr Top Med Chem* 2008; 8(1):34-7). Targeting Aβ42 at the level of γ-secretase activity must, however, be conducted with caution since γ-secretase catalyses proteolysis of many proteins, which have important physiological functions. Among its many substrates is the Notch receptor family, which signaling is essential for many different cell fate determination processes e.g. during embryogenesis and in the adult. As such, Aβ42 lowering strategies at the level of γ-secretase must be compatible with maintained Notch signaling.

It has been suggested that it is possible to combine γ-secretase interference and lowered Aβ42 production without obtaining toxic side effects due to impaired Notch signaling. There have, for instance, been reports which postulate that allosteric modulation of γ-secretase combines lowered Aβ42 production with maintained Notch signaling (Weggen et al. Nature 414(6860), 212-216 (2003); Kounnas et al. Neuron 67, 769-780 (2010); Zettl et al. Trends Pharmacol. Sci. 31, 402-410 (2010)). In addition, a number of compounds interfering with γ-secretase and Aβ production have been suggested in, e.g., WO2005/054193, WO2005/013985, WO2004/073705, WO2007/135969, WO2007/139149, WO2005/115990, WO2008/097538, WO2008/099210, WO2008/100412, WO2007/125364, WO2009/020580, WO2009/087127, WO2009/103652, WO2010/053438, WO2010/132015, WO2010/083141, WO2010/052199, WO2011/006903, WO2011/014535, WO2011/092272, WO2011/086098, WO2011/086099 and WO2012/009309.

The present invention relates to novel compounds, which inhibit the Aβ40 and Aβ42 production, increase Aβ37 and Aβ38 levels and maintain Notch signaling. These compounds are therefore useful in the prevention and/or treatment of, e.g. Alzheimer's Disease (AD). The compounds have preferably an improved pharmacokinetic and pharmacodynamic profile compared to known compounds, such as improved selectivity, an improved absorbtion after oral administration, improved first passage and faster onset of action, as well as reduced side effects, such as no or a minimized impairment on Notch signaling. Passage of the blood-brain barrier is preferably improved as well.

DISCLOSURE OF THE INVENTION

The present invention is directed to compounds according to formula (I)

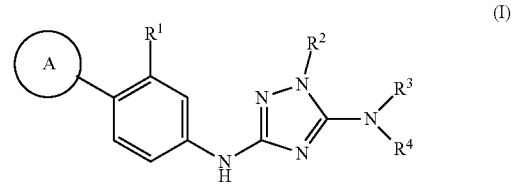

wherein:
A is 5- or 6-membered heteroaryl ring comprising at least one nitrogen atom, wherein the 5- or 6-membered heteroaryl ring is optionally substituted with one substituent selected from the group consisting of $C_{1-3}$-alkyl, $C_{1-3}$-alkoxy and halo;

$R^1$ is hydrogen, $C_{1-3}$-alkoxy, $C_{1-3}$-alkyl, cyano or halo;
$R^2$ is $C_{1-6}$-alkyl (optionally substituted with one or more substituents independently selected from the group consisting of hydroxy, halo and cyano), $C_{3-7}$-cycloalkyl-$C_{1-3}$-alkyl, heterocyclyl-$C_{1-3}$-alkyl or phenyl-$C_{1-3}$-alkyl (wherein any $C_{3-7}$-cycloalkyl, heterocyclyl and phenyl rings are optionally substituted with one or more substituents independently selected from the group consisting of fluoro and $C_{1-3}$-alkyl); and
$R^3$ and $R^4$ are each independently selected from the group consisting of hydrogen, $C_{1-6}$-alkyl, fluoro-$C_{1-6}$-alkyl, hydroxy-$C_{1-6}$-alkyl, $C_{3-7}$-cycloalkyl, $C_{3-7}$-cycloalkyl-$C_{1-3}$-alkyl, phenyl and phenyl-$C_{1-3}$-alkyl;
as a free base or a pharmaceutically acceptable salt thereof; provided that the compound is not $N^5$-(2-chlorophenyl)-$N^3$-[3-methoxy-4-(4-methyl-1H-imidazol-1-yl)phenyl]-1-methyl-1H-1,2,4-triazole-3,5-diamine.

It has surprisingly been found that these compounds, especially with an $R^4$ substituent having an aromatic ring or a saturated cycloalkyl ring attached to a methylene group, show excellent pIC50 values. It is believed that the $R^4$-group improved selectivity for Aβ42 and can be used to reduce the ratio Aβ 42/40 peptides. The compounds are expected to have improved blood-brain passage and thus an improved pharmacokinetic and dynamic profile, such as a faster onset of action and reduced side effects. This is especially true for the compounds, wherein $R^2$ is the more hydrophilic alcohol-substituent.

In one embodiment of the invention, A is a 5- or 6-membered heteroaryl ring selected from the group consisting of pyridinyl, pyridazinyl, pyrimidinyl, pyrazinyl, triazinyl, imidazolyl, thiazolyl, isothiazolyl, pyrryl, oxazolyl, isoxazolyl, pyrazolyl, triazolyl, tetrazolyl and thiadiazolyl, wherein the ring is optionally substituted with one $C_{1-3}$-alkyl substituent.

In another embodiment, A is selected from the group consisting of pyridinyl, pyridazinyl, pyrimidinyl, imidazolyl, thiazolyl, oxazolyl, pyrazolyl and triazolyl, and is substituted with one methyl substituent.

In yet another embodiment, A is imidazolyl substituted with methyl. In yet another embodiment, A is 4-methyl-1H-imidazol-1-yl.

In one embodiment, $R^1$ is hydrogen, methoxy or cyano. In another embodiment, $R^1$ is methoxy.

In one embodiment, $R^2$ is $C_{1-6}$-alkyl, which is optionally substituted with one or more substituents independently selected from the group consisting of hydroxy, halo and cyano, or is phenyl-$C_{1-3}$-alkyl.

In another embodiment, $R^2$ is $C_{1-4}$-alkyl, which is optionally substituted with one substituent independent selected from the group consisting of hydroxy, halo and cyano, or is phenyl-$C_{1-3}$-alkyl, wherein phenyl is optionally substituted with one or more fluoro substituents.

In another embodiment, $R^2$ is $C_{1-4}$-alkyl, which is optionally substituted with one hydroxy substituent, or is phenyl-$C_{1-2}$-alkyl.

In another embodiment, $R^2$ is methyl, 2-methylpropyl, 2-hydroxy-2-methylpropyl or benzyl.

In a further embodiment, $R^2$ is hydroxy-$C_{1-4}$-alkyl or phenyl-$C_{1-2}$-alkyl.

In a preferred embodiment, $R^2$ is hydroxy-$C_{1-4}$-alkyl, and most preferably 2-hydroxy-2-methylpropyl.

In another preferred embodiment, $R^2$ is phenyl-$C_{1-2}$-alkyl, and most preferably benzyl.

In one embodiment, $R^3$ and $R^4$ are each independently selected from the group consisting of hydrogen, $C_{1-6}$-alkyl, hydroxy-$C_{1-6}$-alkyl, $C_{3-7}$-cycloalkyl-$C_{1-3}$-alkyl and phenyl-$C_{1-3}$-alkyl, wherein any $C_{3-7}$-cycloalkyl and phenyl rings are optionally substituted with one or more substituents independently selected from the group consisting of fluoro and $C_{1-3}$-alkyl.

In another embodiment, $R^3$ and $R^4$ are each independently selected from the group consisting of hydrogen, $C_{1-3}$-alkyl, hydroxy-$C_{1-4}$-alkyl, $C_{3-7}$-cycloalkyl-$C_{1-3}$-alkyl and phenyl-$C_{1-2}$-alkyl. In another embodiment, $R^3$ and $R^4$ are each independently hydrogen, methyl, 2-hydroxy-2-methylpropyl, cyclopropylmethyl or benzyl. The benzyl group is preferably not substituted. As shown in WO2011/086099, for example 50, a substituent on the phenyl ring has a negative effect on the binding affinity to the receptor. An improved binding to the receptor is obtained by an R3 or R4 substituent comprising a linker of at least methylene attached to an unsubstituted aromatic ring, such as phenyl or cycloalkyl.

In a preferred embodiment of the invention, A is selected from the group consisting of pyridinyl, pyridazinyl, pyrimidinyl, imidazolyl, thiazolyl, oxazolyl, pyrazolyl and triazolyl, and is substituted with one methyl substituent;
$R^1$ is hydrogen, methoxy or cyano;
$R^2$ is $C_{1-4}$-alkyl, which is optionally substituted with one substituent independent selected from the group consisting of hydroxy, halo and cyano, or is phenyl-$C_{1-3}$-alkyl.
$R^3$ and $R^4$ are each independently selected from the group consisting of hydrogen, $C_{1-6}$-alkyl, hydroxy-$C_{1-6}$-alkyl, $C_{3-7}$-cycloalkyl-$C_{1-3}$-alkyl and phenyl-$C_{1-3}$-alkyl.

In another preferred embodiment of the invention, A is 4-methyl-1H-imidazol-1-yl and $R^1$ is methoxy.

In a further embodiment, the invention relates to compounds according to formula (Ia)

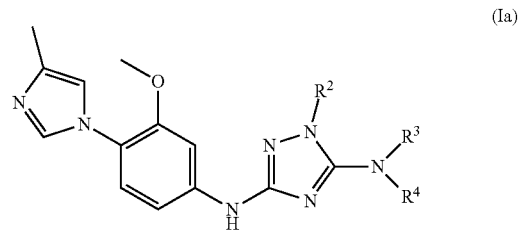

(Ia)

wherein:

$R^2$ is $C_{1-4}$-alkyl, which is optionally substituted with one hydroxy substituent, or is phenyl-$C_{1-2}$-alkyl;

$R^3$ is hydroxy-$C_{1-6}$-alkyl, $C_{3-7}$-cycloalkyl-$C_{1-3}$-alkyl or phenyl-$C_{1-3}$-alkyl; and $R^4$ is hydrogen, $C_{1-3}$-alkyl or $C_{3-7}$-cycloalkyl-$C_{1-3}$-alkyl, as a free base or a pharmaceutically acceptable salt thereof.

In one embodiment, the invention relates to a compound of formula (Ia), wherein $R^2$ is hydroxy-$C_{1-4}$-alkyl or phenyl-$C_{1-2}$-alkyl.

In a preferred embodiment, the invention relates to a compound of formula (Ia), wherein $R^2$ is hydroxy-$C_{1-4}$-alkyl, most preferably 2-hydroxy-2-methylpropyl. Improved uptake in the gastrointestinal tract can be obtained by the addition of a more hydrophilic group, such as an alcohol group.

In another preferred embodiment, the invention relates to a compound of formula (Ia), wherein $R^2$ is phenyl-$C_{1-2}$-alkyl, most preferably benzyl.

In one embodiment, the invention relates to a compound of formula (Ia), wherein:
$R^2$ is 2-hydroxy-2-methylpropyl;
$R^3$ is cyclopropylmethyl, benzyl or 2-hydroxy-2-methylpropyl; and
$R^4$ is hydrogen, methyl or cyclopropylmethyl.

In another embodiment, the invention relates to a compound of formula (Ia), wherein:
$R^2$ is benzyl;
$R^3$ is cyclopropylmethyl, benzyl or 2-hydroxy-2-methylpropyl; and
$R^4$ is hydrogen, methyl or cyclopropylmethyl.

In another embodiment, the invention relates to a compound of formula (I), or a pharmaceutically acceptable salt thereof, selected from the group consisting of:
$N^5$-(Cyclopropylmethyl)-$N^3$-[3-methoxy-4-(4-methyl-1H-imidazol-1-yl)phenyl]-1-methyl-1H-1,2,4-triazole-3,5-diamine;
5-N,5-N-Bis(cyclopropylmethyl)-3-N-[3-methoxy-4-(4-methyl-1H-imidazol-1-yl)phenyl]-1-methyl-1H-1,2,4-triazole-3,5-diamine;
5-N-(Cyclopropylmethyl)-3-N-[3-methoxy-4-(4-methyl-1H-imidazol-1-yl)phenyl]-1-(2-methylpropyl)-1H-1,2,4-triazole-3,5-diamine;
1-[(1-Benzyl-3-{[3-methoxy-4-(4-methyl-1H-imidazol-1-yl)phenyl]amino}-1H-1,2,4-triazol-5-yl)(methyl)amino]-2-methylpropan-2-ol;
1-{5-[(Cyclopropylmethyl)(methyl)amino]-3-{[3-methoxy-4-(4-methyl-1H-imidazol-1-yl)-phenyl]amino}-1H-1,2,4-triazol-1-yl}-2-methylpropan-2-ol;
1-[5-(Benzylamino)-3-{[3-methoxy-4-(4-methyl-1H-imidazol-1-yl)phenyl]amino}-1H-1,2,4-triazol-1-yl]-2-methylpropan-2-ol; and
1-{5-[Benzyl(methyl)amino]-3-{[3-methoxy-4-(4-methyl-1H-imidazol-1-yl)phenyl]amino}-1H-1,2,4-triazol-1-yl}-2-methylpropan-2-ol.

In another aspect, the invention relates to a compound of formula (I) (including compounds of formula (Ia)), or a pharmaceutically acceptable salt thereof, for use in therapy.

In another aspect, the invention relates to a compound of formula (I), or a pharmaceutically acceptable salt thereof, for use in the treatment and/or prevention of an Aβ-related pathology.

In one embodiment, the invention relates to a compound of formula (I), or a pharmaceutically acceptable salt thereof, for use in the treatment and/or prevention of an Aβ-related pathology selected from the group consisting of Down's syndrome, a β-amyloid angiopathy, cerebral amyloid angiopathy, hereditary cerebral hemorrhage, a disorder associated with cognitive impairment, MCI ("mild cognitive impairment"), Alzheimer's disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy and cortical basal degeneration.

In another embodiment, the invention relates to a compound of formula (I), or a pharmaceutically acceptable salt thereof, for use in the treatment and/or prevention of Alzheimer's disease.

In another aspect, the invention relates to the use of a compound of formula (I), or a pharmaceutically acceptable salt thereof, in the manufacture of a medicament for the treatment and/or prevention of an Aβ-related pathology.

In another aspect, the invention relates to a method of treating and/or preventing an Aβ-related pathology in a mammal, comprising administering to said mammal a therapeutically effective amount of the compound of formula (I), or a pharmaceutically acceptable salt thereof.

In another aspect, the invention relates to a pharmaceutical composition comprising a therapeutically effective amount of a compound of formula (I), or a pharmaceutically acceptable salt thereof, in association with a pharmaceutically acceptable excipient, carrier or diluent. In one aspect, the invention relates to the pharmaceutical composition for use in therapy.

The treatment of Aβ-related pathology defined herein may be applied as a sole therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents, or atypical antipsychotic agents. Cognitive enhancing agents, memory enhancing agents and acetyl choline esterase inhibitors include onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX).

Such conjoint treatment may be achieved by way of the simultaneous, sequential or separate dosing of the individual components of the treatment. Such combination products employ the compounds, or pharmaceutically acceptable salts thereof, of the invention.

In another aspect, the invention relates to a pharmaceutical composition comprising (i) a compound of formula (I), or a pharmaceutically acceptable salt thereof, (ii) an additional therapeutic agent, or a pharmaceutically acceptable salt thereof, and (iii) a pharmaceutically acceptable excipient, carrier or diluent.

In another aspect, the invention relates to a pharmaceutical composition comprising (i) a compound of formula (I), or a pharmaceutically acceptable salt thereof, (ii) at least one agent selected from the group consisting of acetyl cholinesterase inhibitors, anti-inflammatory agents, cognitive enhancing agents, memory enhancing agents, and atypical antipsychotic agents, and (iii) a pharmaceutically acceptable excipient, carrier or diluent.

In one aspect, the invention relates to a pharmaceutical composition comprising (i) a compound of formula (Ia), or a pharmaceutically acceptable salt thereof, (ii) at least one agent selected from the group consisting of onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX), and (iii) a pharmaceutically acceptable excipient, carrier or diluent.

Additional conventional chemotherapy or therapy may include one or more of the following categories of agents: (i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine and venlafaxine.

(ii) atypical antipsychotics such as quetiapine.

(iii) antipsychotics such as amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine and ziprasidone.

(iv) anxiolytics such as alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam and zolazepam.

(v) anticonvulsants such as carbamazepine, clonazepam, ethosuximide, felbamate, fosphenytoin, gabapentin, lacosamide, lamotrogine, levetiracetam, oxcarbazepine, phenobarbital, phenytoin, pregabaline, rufinamide, topiramate, valproate, vigabatrine and zonisamide.

(vi) Alzheimer's therapies such as donepezil, memantine, rivastigmine, galantamine and tacrine.

(vii) Parkinson's therapies such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase.

(viii) migraine therapies such as almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan and zomitriptan.

(ix) stroke therapies such as abciximab, activase, NXY-059, citicoline, crobenetine, desmoteplase, repinotan, clopidogrel, eptifibatide, minocycline and traxoprodil.

(x) urinary incontinence therapies such as darafenacin, falvoxate, oxybutynin, propiverine, robalzotan, solifenacin and tolterodine.

(xi) neuropathic pain therapies including for example lidocain and capsaicin, and anticonvulsants such as gabapentin and pregabalin, and antidepressants such as duloxetine, venlafaxine, amitriptyline and klomipramine.

(xii) nociceptive pain therapies such as paracetamol; NSAIDS such as diclofenac, loxoprofen, naproxen, ketoprofen, ibuprofen, nabumeton, meloxicam and piroxicam; coxibs such as celecoxib, etoricoxib, lumiracoxib, rofecoxib, valdecoxib and parecoxib; and opioids such as morphine, oxycodone, buprenorfin and tramadol.

(xiii) insomnia therapies such as agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon and zolpidem.

(xiv) mood stabilizers such as carbamazepine, divalproex, gabapentin, lamotrigine, lithium, olanzapine, quetiapine, valproate, valproic acid and verapamil.

Such combination products employ the compounds of this invention within the dosage range described herein and the other pharmaceutically active compound or compounds within approved dosage ranges and/or the dosage described in the publication reference.

DEFINITIONS

The definitions set forth in this application are intended to clarify terms used throughout this application. The term "herein" means the entire application.

As used herein, the term "$C_{1-6}$-alkyl", used alone or as a suffix or prefix, is intended to include both branched and straight chain saturated aliphatic hydrocarbon groups having from 1 to 6 carbon atoms. Examples of $C_{1-6}$-alkyl include, but are not limited to, methyl, ethyl, n-propyl, i-propyl, n-butyl, i-butyl, sec-butyl, tert-butyl, pentyl and hexyl. Similarly, the term "$C_{1-3}$-alkyl" denotes alkyl having 1, 2 or 3 carbon atoms.

As used herein, the term "fluoro-$C_{1-6}$-alkyl", used alone or as a suffix or prefix, is intended to include both branched and straight chain saturated aliphatic hydrocarbon groups, having at least one fluoro substituent and having from 1 to 6 carbon atoms. Examples of fluoro-$C_{1-6}$-alkyl include, but are not limited to, fluoromethyl, difluoromethyl, trifluoromethyl, 1-fluoroethyl and 3-fluoropropyl.

As used herein, the term "hydroxy-$C_{1-6}$-alkyl", used alone or as a prefix, refers to a $C_{1-6}$-alkyl radical, as defined above, which is substituted with at least one hydroxy group. Exemplary hydroxy-$C_{1-6}$-alkyl groups include hydroxymethyl, 2-hydroxyethyl, 2-hydroxypropyl and 1-hydroxy-1-methylethyl.

As used herein, the term "$C_{1-3}$-alkoxy", used alone or as a suffix och prefix, refers to a $C_{1-3}$-alkyl radical which is attached to the remainder of the molecule through an oxygen atom. Examples of $C_{1-3}$-alkoxy include methoxy, ethoxy, n-propoxy and isopropoxy.

As used herein, "halo" or "halogen" refers to fluoro, chloro, bromo, and iodo.

As used herein, the term "heteroaryl" refers to a monocyclic heteroaromatic ring having 5 or 6 ring members and wherein at least one ring member is nitrogen. Examples include pyridinyl, pyridazinyl, pyrimidinyl, pyrazinyl, triazinyl, imidazolyl, thiazolyl, isothiazolyl, pyrryl, oxazolyl, isoxazolyl, pyrazolyl, triazolyl, tetrazolyl and thiadiazolyl.

As used herein, the term "$C_{3-7}$-cycloalkyl", used alone or as suffix or prefix, denotes a cyclic saturated alkyl group having a ring size from 3 to 7 carbon atoms and includes cyclopropyl, cyclobutyl, cyclopentyl, cyclohexyl and cycloheptyl.

As used herein, the term "$C_{3-7}$-cycloalkyl-$C_{1-3}$-alkyl" refers to a $C_{3-7}$-cycloalkyl group that is attached through a $C_{1-3}$-alkyl radical. Examples of $C_{3-7}$-cycloalkyl-$C_{1-3}$-alkyl include cyclopropylmethyl, 2-cyclopropylethyl and 2-cyclohexylethyl.

As used herein, the term "heterocyclyl" denotes a saturated monocyclic ring containing 3 to 7 ring atoms wherein 1 or 2 ring atoms are independently selected from nitrogen, sulphur and oxygen, and the remaining ring atoms are carbon. When present, the sulphur atom may be in an oxidized form (i.e., S=O or O=S=O). Examples of heterocyclyl include, but are not limited to, piperidinyl, piperazinyl, homopiperazinyl, azetidinyl, oxetanyl, morpholinyl, pyrrolidinyl, tetrahydropyranyl, tetrahydrofuranyl, tetrahydrothiopyranyl, tetrahydro-thiopyran 1-oxide and tetrahydro-thiopyran 1,1-dioxide.

As used herein, the term "heterocyclyl-$C_{1-3}$-alkyl" refers to a heterocyclyl group that is attached through a $C_{1-3}$-alkyl radical. Examples of heterocyclyl-$C_{1-3}$-alkyl include tetrahydropyran-4-ylmethyl, piperidin-4-ylmethyl, tetrahydrofuran-2-ylmethyl, oxetan-3-ylmethyl, 2-(4-morpholinyl)methyl and 2-(piperazin-1-yl)ethyl.

As used herein, the term "phenyl-$C_{1-3}$-alkyl" refers to a phenyl group that is attached through a $C_{1-3}$-alkyl radical. Examples of phenyl-$C_{1-3}$-alkyl include phenylmethyl (benzyl), 1-phenylethyl and 2-phenylethyl.

As used herein, the term "optional" or "optionally" means that the subsequently described event or circumstance may but need not occur, and that the description includes instances where the event or circumstance occurs and instances where it does not.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "protecting group" means temporary substituents protecting a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been extensively reviewed (see, e.g. Jarowicki, K.; Kocienski, P. Perkin Trans. 1, 2001, issue 18, p. 2109).

As used herein, "pharmaceutically acceptable salts" refer to forms of the disclosed compounds, wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

A variety of compounds in the present invention may exist in particular geometric or stereoisomeric forms. The present invention takes into account all such compounds, including tautomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. All chiral, diastereomeric and racemic forms are intended, unless the specific stereochemistry or isomeric form is specifically indicated.

As used herein, "tautomer" means other structural isomers that exist in equilibrium resulting from the migration of a hydrogen atom. For example, keto-enol tautomerism occurs where the resulting compound has the properties of both a ketone and an unsaturated alcohol.

Compounds and pharmaceutically acceptable salts of the invention further include hydrates and solvates thereof.

Compounds and salts described in this specification may be isotopically-labelled compounds (or "radio-labelled"). In that instance, one or more atoms are replaced by an atom having an atomic mass or mass number different from the atomic mass or mass number typically found in nature (i.e., naturally occurring). Examples of suitable isotopes that may be incorporated include $^{2}H$ (also written as "D" for deuterium), $^{3}H$ (also written as "T" for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is used will depend on the specific application of that radio-labelled derivative. For example, for in vitro receptor labelling and competition assays, compounds that incorporate $^{3}H$ or $^{14}C$ are often useful. For radio-imaging applications $^{11}C$ or $^{18}F$ are often useful. In some embodiments, the radionuclide is $^{3}H$. In some embodiments, the radionuclide is $^{14}C$. In some embodiments, the radionuclide is $^{11}C$. And in some embodiments, the radionuclide is $^{18}F$.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The optimum dosage and frequency of administration will depend on the particular condition being treated and its severity; the age, sex, size and weight, diet, and general physical condition of the particular patient; other medication the patient may be taking; the route of administration; the formulation; and various other factors known to physicians and others skilled in the art.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles and/or carrier in compositions and to be administered in methods of the invention.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

Preparation of Compounds

The compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3rd Edition, Wiley-Interscience, New York, 1999. Where necessary, the order of reaction process steps such as introduction of substituents can be altered.

Compounds of the present invention can be synthesized according to scheme 1.

solvent such as dioxane or DMA, and at a temperature in the range of about 20° C. to 170° C. A compound of formula (III) can be further alkylated using an alkylating reagent of formula $R^4X$ where X is described above. The reaction can be performed in the presence of a base such as potassium tert-butoxide or sodium hydride, in a solvent such as DMF, at a temperature in the range of about 0° C. to 100° C. The compound of formula (III) or (IV) is then reacted with an aniline of formula (V) to give a compound of formula (I) under standard Buchwald-Hartwig conditions. Examples of reagents used are palladium(II) acetate as catalyst, Xantphos as ligand, cesium carbonate as base and dioxane as solvent. The reaction is run at temperatures in the range of about 50° C. to 150° C.

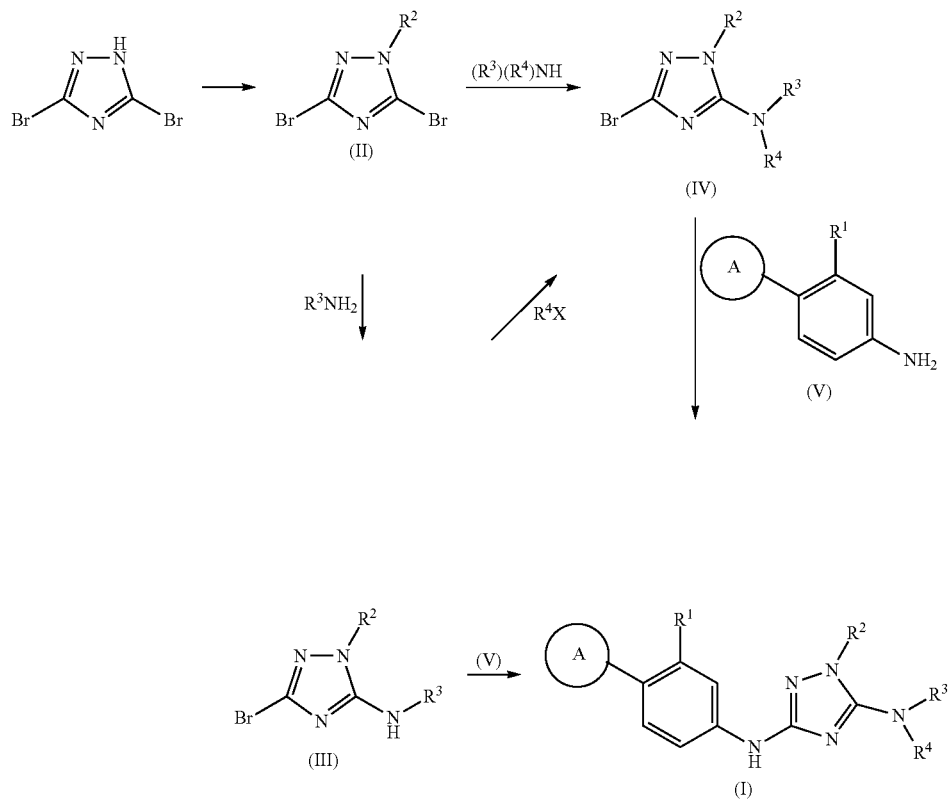

Dibromotriazole is reacted with an alkylating reagent of formula $R^2X$, where X is a leaving group such as chloro, bromo, iodo or sulfonyloxy, to give a compound of formula (II). The reaction is performed in the presence of a base such as potassium alkoxide or sodium hydride at temperatures in the range of about 20° C. to 80° C. Compound (II) is reacted with a primary amine of formula $R^3NH_2$ or secondary amine of formula $(R^3)(R^4)NH$ to give a compound of formula (III) or (IV). The reaction is performed in the presence of a base such as potassium tert-butoxide, potassium carbonate, diisopropylamine or diethylamine, in a

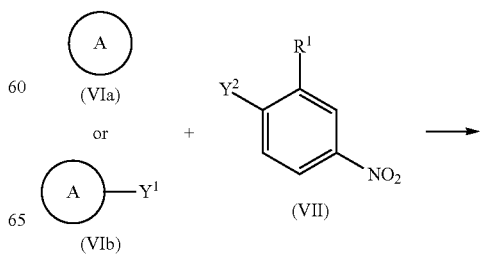

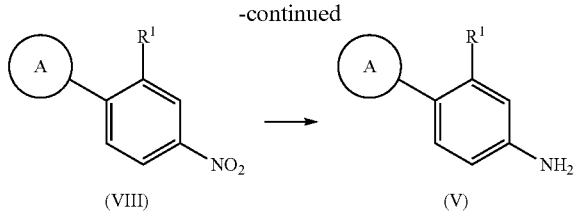

If ring A is attached to the phenyl ring through a nitrogen atom, a heteroaryl compound of formula (VIa) is reacted with a compound of formula (VII) wherein $Y^2$ is fluoro, chloro or bromo, to give a compound of formula (VIII). The reaction is performed in the presence of a base such as potassium carbonate or sodium hydroxide in a solvent such as acetonitrile, DMSO or DMF at temperatures in the range of about 20° C. and 150° C. Alternatively, the reaction can be catalysed by for example Cu(I)iodide.

If ring A is attached to the phenyl ring though a carbon atom, a heteroaryl compound of formula (VIb) wherein $Y^1$ is for example trialkylstannane, boronic acid or boronic ester, is reacted with a compound of formula (VII) wherein $Y^2$ is chlorine, bromine, iodine or triflate, to give a compound of formula (VIII). This reaction is performed under Stille or Suzuki conditions in the presence of for example a palladium catalyst, a ligand and a base.

Alternatively, the heterocyclic ring A can also be formed onto the phenyl ring. For example, a compound of formula (VII) wherein $Y^2$ is —C(O)CH$_2$Br can be transformed in several steps to form an appropriately substituted oxazole ring.

A compound of formula (VIII) can be transformed into a compound of formula (V) using standard conditions, for example catalytic hydrogenation with palladium on charcoal.

General Methods

NMR spectra were recorded on a 400 MHz or 500 MHz NMR spectrometer fitted with a probe of suitable configuration. Spectra were recorded at ambient temperature unless otherwise stated. Chemical shifts are given in ppm downand upfield from TMS (0.00 ppm). The following reference signals were used: TMS δ 0.00, or the residual solvent signal of DMSO-d$_6$ δ 2.50, CD$_3$OD δ 3.30, acetone-d$_6$ 2.04 or CDCl$_3$ δ7.27 (unless otherwise indicated). Resonance multiplicities are denoted s, d, t, q, m, br and app for singlet, doublet, triplet, quartet, multiplet, broad and apparent, respectively.

Preparative or analytical High pressure liquid chromatography (HPLC) was performed on a reversed phase (RP) column. A linear gradient was applied using for example mobile phase A (0.1% Formic Acid in MilliQ H$_2$O or 0.1% NH$_3$ in MilliQ H$_2$O or 10 mM NH$_4$OAc and 5% CH$_3$CN in MilliQ H$_2$O.) and B (CH$_3$OH or CH$_3$CN). Mass spectrometer (MS) analyses were performed in positive and/or negative ion mode using electrospray ionization (ESI+/−), atmospheric pressure photo ionization (APPI+/−) and/or atmospheric pressure chemical ionization (APCI+/−).

Gas chromatography (GC) was performed on a GC equipped with a mass spectrometer (MS) or a flame ionization detector (FID). The MS ion source was either an electron impact (EI) or a chemical ionization (CI, reactant gas methane).

Supercritical Fluid Chromatography (SFC) was performed on a straight phase column. A isocratic flow was applied using mobile phase A (CO$_2$) and for example mobile phase B (MeOH, EtOH or IPA optionally containing DEA).

The compounds have been named using CambridgeSoft MedChem ELN v2.1, the naming tool in reaxys (reaxys.com) or are according to IUPAC convention.

ABBREVIATIONS

DCM dichloromethane
DMA dimethylacetamide
DMF dimethylformamide
EtOAc ethyl acetate
MeOH methanol
MTBE methyl tert-butylether
rt room temperature
THF tetra hydrofuran
TMS tetramethylsilane
Xantphos (5-diphenylphosphanyl-9,9-dimethyl-xanthen-4-yl)-diphenyl-phosphane

EXAMPLES

The compounds described in this specification are further illustrated in the following Examples. These Examples are given by way of illustration only and are non-limiting.

Intermediate 1

3,5-Dibromo-1H-1,2,4-triazole

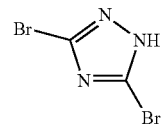

1H-1,2,4-Triazole (3.9 g, 56 mmol) was mixed in water (50 mL) and DCM (15 mL) at 0° C. A solution of dibromine (6.1 mL, 119 mmol) in DCM (15 mL) and a solution of sodium hydroxide (6.78 g, 169 mmol) in water (20 mL) were added dropwise simultaneously while keeping the reaction temperature below 20° C. The mixture was stirred at ambient temperature over night. Hydrochloric acid (conc, 2.0 mL, 66 mmol) was added. The solid was isolated by filtration, washed with water and dried under vacuum to yield the title compound as a solid (8.3 g, 65%).

MS (ESI−) m/z 224 [M−H]−.

Intermediate 2

3,5-Dibromo-1-methyl-1H-1,2,4-triazole

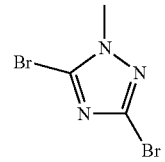

To 3,5-dibromo-1H-1,2,4-triazole (1.0 g, 4.41 mmol) in DMF (9 mL) was added sodium tert-pentoxide (0.485 g, 4.41 mmol). The mixture was stirred for 10 min at rt under nitrogen atmosphere. Iodomethane (0.29 mL, 4.63 mmol) was added and the mixture was stirred at 40° C. for 2 hours. The mixture was poured onto water and extracted with diisopropylether (2×). The organic phase was washed with water (2×), brine and dried over sodium sulfate. The solvents were evaporated to give the title compound as a solid (0.83 g, 78%).

MS (CI) m/z 242 [M+]. $^1$H NMR (500 MHz, CDCl$_3$) δ ppm 3.89 (s, 3H).

Intermediate 3

3-Bromo-N-(cyclopropylmethyl)-1-methyl-1H-1,2,4-triazol-5-amine

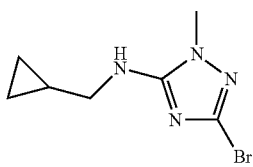

To a solution of 3,5-dibromo-1-methyl-1H-1,2,4-triazole (0.700 g, 2.90 mmol) and cyclopropanemethylamine (0.50 mL, 5.8 mmol) in 1,4-dioxane (2.5 mL) and DMA (1 mL) was added N,N-diisopropylethylamine (0.47 mL, 5.8 mmol). The mixture was heated at 130° C. in a sealed tube for 16 h and then cooled down to rt. Water (5 mL) was added and the resulting solution was extracted with EtOAc (3×15 mL). The combined organic layers were washed with water (10 mL) and brine (10 mL), dried over sodium sulfate and concentrated. The residue was triturated with MTBE to give the title compound as a solid (0.330 g, 49%).

$^1$H NMR (400 MHz, CDCl$_3$): δ ppm 0.23-0.27 (m, 2H), 0.53-0.58 (m, 2H), 1.05-1.16 (m, 1H), 3.23 (dd, 2H), 3.56 (s, 3H), 3.97 (br s, 1H).

Intermediate 4

3-Bromo-N,N-bis(cyclopropylmethyl)-1-methyl-1H-1,2,4-triazol-5-amine

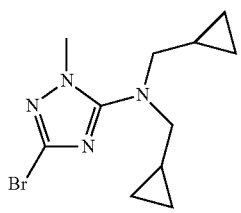 [SMILES: Cn1nc(Br)nc1N(CC1CC1)CC1CC1]

To a solution of 3-bromo-N-(cyclopropylmethyl)-1-methyl-1H-1,2,4-triazol-5-amine (0.189 g, 0.785 mmol) in DMF (5 mL) was added sodium tert-butoxide (75 mg, 0.78 mmol). The mixture was stirred for 15 min at rt and then (bromomethyl)cyclopropane (80 μL, 0.78 mmol) was added dropwise. The reaction mixture was stirred at rt for 24 h. The mixture was diluted with water (20 mL) and extracted with MTBE (3×15 mL). The organic phase was washed with water (15 mL) and brine (15 mL), dried over sodium sulfate and concentrated in vacuo. The residue was purified by column chromatography on a silica gel cartridge eluting with 0% to 15% EtOAc in heptanes to give the title compound as a liquid (0.189 g, 84%).

$^1$H NMR (400 MHz, CDCl$_3$): δ ppm 0.06-0.12 (m, 4H), 0.42-0.49 (m, 4H), 0.85-0.96 (m, 2H), 3.04 (d, 4H), 3.72 (s, 3H).

Intermediate 5

3,5-Dibromo-1-(2-methylpropyl)-1H-1,2,4-triazole

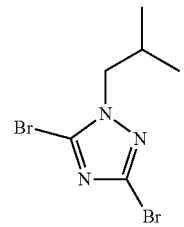

Sodium tert-butoxide (699 mg, 7.27 mmol) was added to a solution of 3,5-dibromo-1H-1,2,4-triazole (1.5 g, 6.61 mmol) in DMF (10 mL). The mixture was stirred at rt for 10 minutes. 1-Bromo-2-methylpropane (0.8 mL, 7.27 mmol) was added and the mixture was heated at 50° C. for 4 h and let to rt. Water (100 mL) was added and the mixture was extracted with EtOAc (2×50 mL). The organic phase was washed with brine (50 mL) and dried over sodium sulfate and concentrated to give the title compound as a liquid (1.47 g, 79%).

$^1$H NMR (400 MHz, CDCl$_3$): δ ppm 0.94 (d, 6H), 2.21-2.32 (m, 1H), 3.93 (d, 2H).

Intermediate 6

3-Bromo-N-(cyclopropylmethyl)-1-(2-methylpropyl)-1H-1,2,4-triazol-5-amine

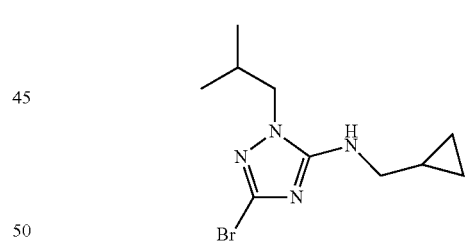

Cyclopropylmethanamine (0.9 mL, 10.41 mmol) and N,N-diisopropylethylamine (1.8 mL, 10.41 mmol) were added to a solution of 3,5-dibromo-1-(2-methylpropyl)-1H-1,2,4-triazole (1.47 g, 5.21 mmol) in dioxane (4 mL) and N,N-dimethylacetamide (2 mL). The mixture was heated to 120° C. overnight and left to reach rt. The mixture was dissolved in EtOAc (150 mL), washed with water (3×50 mL) and brine (50 mL). The organic phase was dried over sodium sulfate and concentrated. The residue was purified on a silica gel cartridge eluting with gradients of EtOAc in heptane. The residue was triturated with MTBE to give the title compound as a solid (507 mg, 35%).

$^1$H NMR (400 MHz, CDCl$_3$): δ ppm 0.22-0.26 (m, 2H), 0.52-0.57 (m, 2H), 0.95 (d, 6H), 1.05-1.15 (m, 1H), 2.13-2.24 (m, 1H), 3.23 (dd, 2H), 3.58 (d, 2H), 3.92 (t, 1H).

Intermediate 7

1-Benzyl-3,5-dibromo-1H-1,2,4-triazole

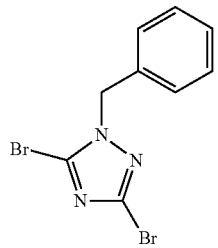 [SMILES: Brc1nc(Br)n(Cc2ccccc2)n1]

Sodium tert-butoxide (932 mg, 9.70 mmol) was added to a solution of 3,5-dibromo-1H-1,2,4-triazole (2.0 g, 8.82 mmol) in DMF (15 mL) and stirred at rt for 10 minutes. Benzyl bromide (1.15 mL, 9.70 mmol) was added and the mixture was stirred at rt overnight. Water (100 mL) was added and the mixture was extracted with EtOAc (2×50 mL). The organic phase was washed with brine (50 mL), dried over sodium sulfate, and concentrated to give the title compound as a liquid (2.69 g, 96%).

$^1$H NMR (400 MHz, CDCl$_3$): δ ppm 5.30 (s, 2H), 7.29-7.39 (m, 5H).

Intermediate 8

2-Benzyl-5-bromo-N-(2-methylallyl)-1,2,4-triazol-3-amine

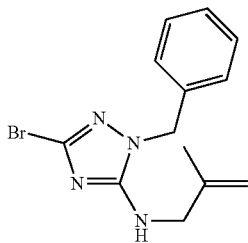 [SMILES: C=C(C)CNc1nc(Br)nn1Cc1ccccc1]

2-Methylallylamine (1.55 mL, 16.97 mmol) and N,N-diisopropylethylamine (2.9 mL, 16.97 mmol) were added to a solution of 1-benzyl-3,5-dibromo-1H-1,2,4-triazole (2.69 g, 8.49 mmol) in dioxane (4 mL) and DMA (2 mL). The mixture was heated to 120° C. overnight in a sealed tube. EtOAc (150 mL) was added and the mixture was washed with water (3×50 mL) and brine (50 mL). The organic phase was dried over sodium sulfate, and concentrated. The residue was purified on a silica gel cartridge using eluting with gradients of EtOAc in heptane to give the title compound as a liquid (2.47 g, 95%).

$^1$H NMR (400 MHz, CDCl$_3$): δ ppm 1.63 (s, 3H), 3.83 (d, 2H), 3.92 (t, 1H), 4.58 (br s, 1H), 4.74 (t, 1H), 5.07 (s, 2H), 7.21-7.23 (m, 2H), 7.29-7.39 (m, 3H).

Intermediate 9

1-[(2-Benzyl-5-bromo-1,2,4-triazol-3-yl)-methyl-amino]-2-methyl-propan-2-ol

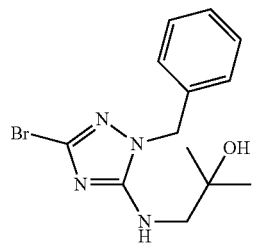 [SMILES: CC(C)(O)CNc1nc(Br)nn1Cc1ccccc1]

THF (25 mL) was added to a solution of mercuric acetate (4.61 g, 14.47 mmol) in water (25 mL) under nitrogen. The flask was covered with aluminum foil and then a solution of 2-benzyl-5-bromo-N-(2-methylallyl)-1,2,4-triazol-3-amine in THF (25 mL) was added. The mixture was stirred at rt overnight. Sodium borohydride (3.04 g, 80.40 mmol) was added portionwise at 0° C. The mixture was left to reach rt and stirred for 1 h. Water (150 mL) was added and the mixture was extracted with EtOAc (3×50 mL). The organic phase was washed with brine (50 mL), dried over sodium sulfate, and concentrated. The residue was purified on a silica gel cartridge eluting with gradients of EtOAc in heptane as eluent to give the title compound as a liquid (1.90 g, 73%).

$^1$H NMR (400 MHz, CDCl$_3$): δ ppm 1.11 (s, 6H), 3.28 (d, 2H), 4.28 (t, 1H), 5.07 (s, 2H), 7.23-7.27 (m, 2H), 7.31-7.39 (m, 3H).

Intermediate 10

1-[(1-Benzyl-3-bromo-1H-1,2,4-triazol-5-yl)(methyl)amino]-2-methylpropan-2-ol

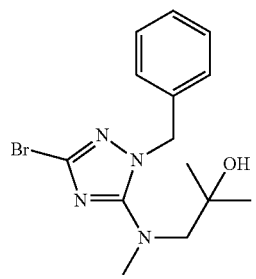 [SMILES: CN(CC(C)(C)O)c1nc(Br)nn1Cc1ccccc1]

Iodomethane (0.47 mL, 7.56 mmol) was added dropwise at 0° C. to a solution of 1-[(2-benzyl-5-bromo-1,2,4-triazol-3-yl)-methyl-amino]-2-methyl-propan-2-ol (1.64 g, 5.04 mmol) and potassium tert-butoxide in DMF (15 mL). The mixture was stirred at rt for 2 h. Water (100 mL) was added and the mixture was extracted with EtOAc (3×50 mL). The organic phase was washed with brine (2×50 mL), dried over sodium sulfate, and concentrated in vacuo. The residue was purified on a silica gel cartridge eluting with gradients of EtOAc in heptane to give the title compound as a liquid (1.26 g, 74%).

¹H NMR (400 MHz, CDCl₃): δ ppm 1.07 (s, 6H), 3.01 (s, 3H), 3.33 (s, 2H), 5.27 (s, 2H). 7.19-7.21 (m, 2H), 7.29-7.38 (m, 3H).

Intermediate 11

3,5-Dibromo-1-(2-methylallyl)-1H-1,2,4-triazole

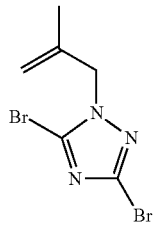

To 3,5-dibromo-1H-1,2,4-triazole (1.5 g, 6.61 mmol) in DMF (13 mL) was added sodium tert-pentoxide (0.728 g, 6.61 mmol) and the mixture was stirred for 10 min at rt under nitrogen atmosphere. 3-Bromo-2-methylprop-1-ene (0.667 mL, 6.61 mmol) was added and the mixture was stirred at 40° C. for 2 hours. The mixture was poured onto water and extracted with diisopropylether (2×). The organic phase was washed with water (2×), brine and dried over sodium sulfate. The solvents were evaporated to give the title compound as a liquid (1.70 g, 91%).

GCMS (CI) m/z 281 [M⁺]. ¹H NMR (400 MHz, CDCl₃) δ ppm 1.74 (d, 3H) 4.69 (s, 2H) 4.81-4.86 (m, 1H) 5.05 (dd, 1H).

Intermediate 12

1-(3,5-Dibromo-1H-1,2,4-triazol-1-yl)-2-methylpropan-2-ol

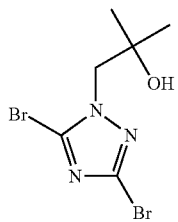

To a solution of mercuric acetate (1.827 g, 5.73 mmol) in water (15 mL), THF (15 mL) was added. The reaction flask was covered with aluminum foil. A solution of 3,5-dibromo-1-(2-methylallyl)-1H-1,2,4-triazole (0.895 g, 3.19 mmol) in THF (15 mL) was added under nitrogen atmosphere. The mixture was stirred at rt for 16 hours. Sodium borohydride (1.20 g, 31.9 mmol) was added in portions and the mixture was stirred for 1 hour. The mixture was diluted with water and extracted with EtOAc. The organic layer was washed with brine, dried over sodium sulfate and concentrated in vacuum to give the title compound as a liquid (0.91 g, 96%).

MS (ESI⁺) m/z 300 [M+H]⁺. ¹H NMR (400 MHz, CDCl₃) δ ppm 1.28 (s, 6H) 4.15 (s, 2H).

Intermediate 13

1-{3-Bromo-5-[(cyclopropylmethyl)amino]-1H-1,2,4-triazol-1-yl}-2-methylpropan-2-ol

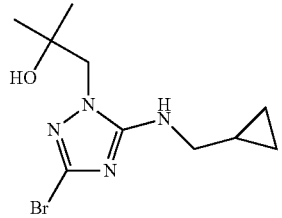 [SMILES: CC(C)(O)Cn1nc(Br)nc1NCC1CC1]

1-(Dibromo-1H-1,2,4-triazol-1-yl)-2-methylpropan-2-ol (538 mg, 1.8 mmol), dioxane (5 mL), dimethylacetamide (0.5 mL), diisopropylethylamine (0.63 mL, 3.6 mmol), and cyclopropylmethanamine (0.31 mL, 3.6 mmol) were added to a pressure-resistant tube. The tube was sealed and heated to 120° C. for 17 h. The mixture was diluted with EtOAc (100 mL) and the mixture was washed with water (3×15 mL), brine (15 mL), dried over magnesium sulfate and concentrated. The residue was triturated with heptanes: EtOAc 90:10 to give the title compound as a solid (314 mg, 60%).

¹H NMR (400 MHz, CDCl₃): δ ppm 0.19-0.24 (m, 2H), 0.49-0.54 (m, 2H), 1.03-1.14 (m, 1H), 1.31 (s, 6H), 1.90 (s, 1H), 3.19 (dd, 2H), 3.84 (s, 2H), 5.41-5.47 (m, 1H).

Intermediate 14

1-{3-Bromo-5-[(cyclopropylmethyl)(methyl)amino]-1H-1,2,4-triazol-1-yl}-2-methylpropan-2-ol

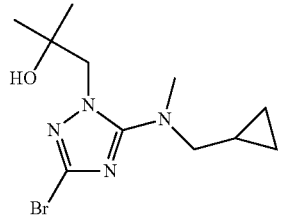 [SMILES: CN(CC1CC1)c1nc(Br)nn1CC(C)(C)O]

1-{3-Bromo-5-[(cyclopropylmethyl)amino]-1H-1,2,4-triazol-1-yl}-2-methylpropan-2-ol (304 mg, 1.05 mmol) was dissolved in dimethylformamide (6 mL) and the solution was cooled to 0° C. Potassium tert-butoxide (353 mg, 3.15 mmol) and iodomethane (0.20 mL, 3.15 mmol) were added. The mixture was stirred at rt for 2.5 h. EtOAc (60 mL) and water (10 mL) were added. The organic layer was washed with brine (3×10 mL), dried over magnesium sulfate and concentrated. The residue was purified on a silica gel cartridge eluting with gradients of EtOAc in heptanes to give the title compound as a liquid (121 mg, 38%).

¹H NMR (400 MHz, CDCl₃): δ ppm 0.12-0.16 (m, 2H), 0.51-0.56 (m, 2H), 0.89-1.00 (m, 1H), 1.19 (s, 6H), 2.90 (s, 3H), 2.97 (d, 2H), 3.96 (s, 2H), 4.01 (s, 1H).

Intermediate 15

1-[5-(Benzylamino)-3-bromo-1H-1,2,4-triazol-1-yl]-2-methylpropan-2-ol

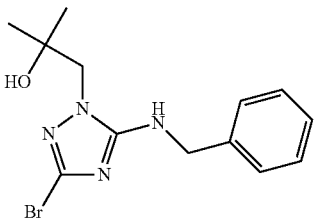 [SMILES: CC(C)(O)Cn1nc(Br)nc1NCc1ccccc1]

Benzylamine (0.4 mL, 3.68 mmol) and N,N-diisopropylethylamine (0.7 mL, 3.68 mmol) were added to a solution of 1-(dibromo-1H-1,2,4-triazol-1-yl)-2-methylpropan-2-ol (550 mg, 1.84 mmol) in dioxane (2 mL) and DMA (1 mL). The reaction mixture was heated to 120° C. overnight in a sealed tube. The mixture was diluted with EtOAc (100 mL), washed with water (3×50 mL) and brine (50 mL). The organic phase was dried over sodium sulfate, and concentrated. The residue was purified on a silica gel cartridge eluting with gradients of EtOAc in heptane to give the title compound as a liquid (554 mg, 93%).

$^1$H NMR (400 MHz, CDCl$_3$): δ ppm 1.28 (s, 6H), 2.87 (s, 1H), 3.84 (s, 2H), 4.52 (d, J=5.6 Hz, 2H), 5.76 (t, J=5.3 Hz, 1H), 7.27-7.34 (m, 5H).

Intermediate 16

1-{5-[Benzyl(methyl)amino]-3-bromo-1H-1,2,4-triazol-1-yl}-2-methylpropan-2-ol

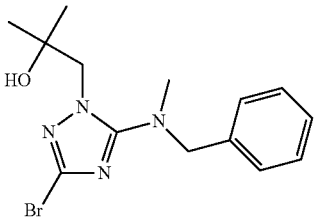 [SMILES: CN(Cc1ccccc1)c1nc(Br)nn1CC(C)(C)O]

N-Benzylmethylamine (0.25 mL, 2.27 mmol) and N,N-diisopropylethylamine (0.4 mL, 2.27 mmol) were added to a solution of 1-(dibromo-1H-1,2,4-triazol-1-yl)-2-methylpropan-2-ol (340 mg, 1.14 mmol) in dioxane (2 mL) and DMA (1 mL). The mixture was heated to 120° C. overnight in a sealed vial. EtOAc (100 mL) was added and the mixture washed with water (3×50 mL) and brine (50 mL). The organic phase was dried over sodium sulfate, and concentrated. The residue was purified on a silica gel cartridge eluting with gradients of EtOAc in heptane to give the title compound as a liquid (252 mg, 65%).

$^1$H NMR (400 MHz, CDCl$_3$): δ ppm 1.15 (s, 6H), 2.82 (s, 3H), 3.86 (s, 1H), 3.88 (s, 2H), 4.31 (s, 2H), 7.26-7.38 (m, 5H).

Example 1

N$^5$-(Cyclopropylmethyl)-N$^3$-[3-methoxy-4-(4-methyl-1H-imidazol-1-yl)phenyl]-1-methyl-1H-1,2,4-triazole-3,5-diamine

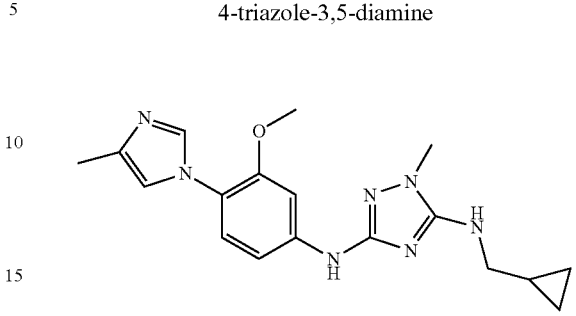

3-Bromo-N-(cyclopropylmethyl)-1-methyl-1H-1,2,4-triazol-5-amine (0.100 g, 0.432 mmol) was dissolved in 1,4-dioxane (4 mL). Cesium carbonate (0.563 g, 1.728 mmol), Xantphos (52 mg, 0.091 mmol), 3-methoxy-4-(4-methyl-1H-imidazol-1-yl)aniline dihydrochloride (0.119 g, 0.432 mmol) and palladium(II) acetate (15 mg, 0.066 mmol) were added. The reaction mixture was stirred at 120° C. for 18 h under nitrogen atmosphere in a sealed vessel. The mixture was allowed to reach rt, filtered through diatomaceous earth and concentrated. The residue was dissolved in DCM (15 mL) and washed with water (10 mL). The organic layer was dried over sodium sulfate and concentrated. The residue product was purified on a silica gel cartridge eluting with gradients of methanol in DCM. The residue was purified using a C18 cartridge eluting with gradients of methanol and water. The residue was triturated with acetonitrile to give the title compound as a solid 40 mg (26%).

MS (ESI) m/z 354 [M+H]$^+$. $^1$H NMR (400 MHz, CDCl$_3$): δ ppm 0.27 (dd, 2H), 0.57 (dd, 2H), 1.09-1.18 (m, 1H), 2.28 (s, 3H), 3.22 (dd, 2H), 3.53 (s, 3H), 3.83 (s, 3H), 3.86-3.92 (m, 1H), 6.47 (br s, 1H), 6.83 (br s, 1H), 6.87 (dd, 1H), 7.10 (d, 1H), 7.37 (d, 1H), 7.57 (br s, 1H).

Example 2

5-N,5-N-Bis(cyclopropylmethyl)-3-N-[3-methoxy-4-(4-methyl-1H-imidazol-1-yl)phenyl]-1-methyl-1H-1,2,4-triazole-3,5-diamine

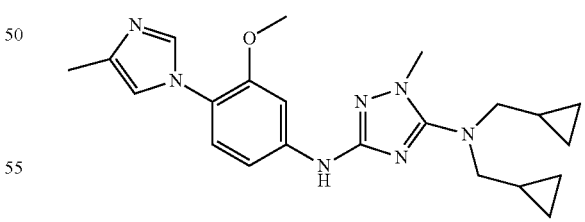

3-Bromo-N,N-bis(cyclopropylmethyl)-1-methyl-1H-1,2,4-triazol-5-amine (0.185 g, 0.648 mmol) was dissolved in 1,4-dioxane (5 mL). Cesium carbonate (0.844 g, 2.59 mmol), Xantphos (79 mg, 0.136 mmol), 3-methoxy-4-(4-methyl-1H-imidazol-1-yl)aniline dihydrochloride (0.179 g, 0.648 mmol) and palladium acetate (22 mg, 0.097 mmol) were added. The mixture was heated at 120° C. for 18 h in a sealed tube under nitrogen atmosphere. The mixture was allowed to reach rt, filtered through diatomaceous earth and concentrated. The residue was dissolved in DCM (15 mL) and washed with water (10 mL). The organic layer was dried over sodium sulfate and concentrated. The residue was purified on a silica gel cartridge eluting with gradients of methanol in DCM. The residue was triturated in acetonitrile to give the title compound as a solid 130 mg (50%).

MS (ESI) m/z 408 [M+H]$^+$. $^1$H NMR (400 MHz, CDCl$_3$): δ ppm 0.10-0.15 (m, 4H), 0.44-0.50 (m, 4H), 0.90-1.00 (m, 2H), 2.28 (s, 3H), 3.04 (d, 4H), 3.69 (s, 3H), 3.84 (s, 3H), 6.48 (s, 1H), 6.83 (s, 1H), 6.86 (dd, 1H), 7.11 (d, 1H), 7.41 (d, 1H), 7.58 (s, 1H).

Example 3

5-N-(Cyclopropylmethyl)-3-N-[3-methoxy-4-(4-methyl-1H-imidazol-1-yl)phenyl]-1-(2-methylpropyl)-1H-1,2,4-triazole-3,5-diamine

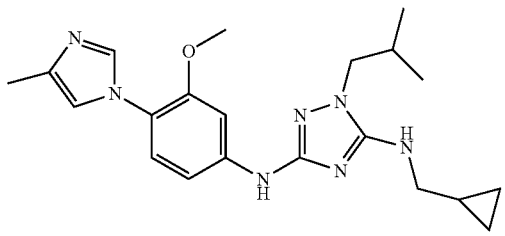 [SMILES: COc1cc(Nc2nc(NCC3CC3)n(CC(C)C)n2)ccc1-n1cnc(C)c1]

3-Bromo-N-(cyclopropylmethyl)-1-(2-methylpropyl)-1H-1,2,4-triazol-5-amine (300 mg, 1.10 mmol), 3-methoxy-4-(4-methyl-1H-imidazol-1-yl)aniline dihydrochloride (303 mg, 1.10 mmol), cesium carbonate (1.43 g, 4.40 mmol), Xantphos (127 mg, 0.22 mmol) and Pd(OAc)$_2$ (49 mg, 0.22 mmol) were dissolved in dioxane (3 mL) and N,N-dimethylacetamide (0.1 mL). The reaction mixture was purged with nitrogen for 10 minutes. The mixture was heated to 120° C. overnight in a sealed vessel. The residue was filtered through diatomaceous earth, washed with methanol and concentrated in vacuo. The residue was purified on a silica gel cartridge eluting with gradients of methanol in DCM. The residue was purified again on a C18 cartridge eluting with gradients of MeOH in water to give the title compound as a solid (80 mg, 20%).

MS (ESI) m/z 396 [M+H]$^+$. $^1$H NMR (400 MHz, CDCl$_3$): ppm 0.24-0.28 (m, 2H), 0.54-0.59 (m 2H), 1.00 (d, 6H), 1.10-1.17 (m, 1H), 2.20-2.27 (m, 1H), 2.29 (s, 3H), 3.23 (m, 2H), 3.55 (d, 2H), 3.80-3.81 (m, 1H), 3.83 (s, 3H), 6.44 (s, 1H), 6.81 (d, 1H), 6.83 (s, 1H), 7.09 (d, 1H), 7.48 (d, 1H), 7.57 (d, 1H).

Example 4

1-[(1-Benzyl-3-{[3-methoxy-4-(4-methyl-1H-imidazol-1-yl)phenyl]amino}-1H-1,2,4-triazol-5-yl)(methyl)amino]-2-methylpropan-2-ol

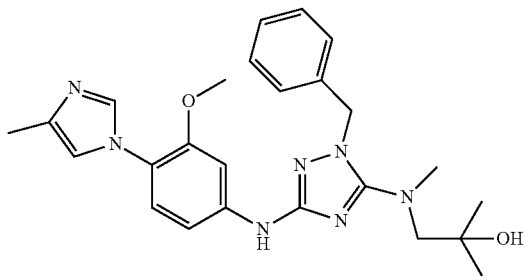 [SMILES: COc1cc(Nc2nc(N(C)CC(C)(C)O)n(Cc3ccccc3)n2)ccc1-n1cnc(C)c1]

1-[(1-Benzyl-3-bromo-1H-1,2,4-triazol-5-yl)(methyl)amino]-2-methylpropan-2-ol (300 mg, 0.88 mmol), 3-methoxy-4-(4-methyl-1H-imidazol-1-yl)aniline dihydrochloride (244 mg, 0.88 mmol), cesium carbonate (1.15 g, 3.52 mmol), Xantphos (102 mg, 0.18 mmol) and Pd(OAc)$_2$ (40 mg, 0.18 mmol) were mixed in dioxane (3 mL) and N,N-dimethylacetamide (0.1 mL). The mixture was purged with nitrogen for 10 minutes. The reaction mixture was stirred in a sealed tube at 120° C. overnight and cooled down to rt. The residue was filtered through diatomaceous earth, washed with methanol and concentrated. The residue was purified on a silica gel cartridge eluting with gradients of MeOH in DCM. The residue was purified again on a 15 g C18 cartridge eluting with gradients of MeOH in water to give the title compound as a solid (73 mg, 18%).

MS (ESI) m/z 462 [M+H]$^+$. $^1$H NMR (400 MHz, CDCl$_3$): ppm 1.15 (s, 6H), 2.28 (s, 3H), 3.07 (s, 3H), 3.35 (s, 2H), 3.78 (s, 3H), 5.23 (s, 2H), 6.42 (s, 1H), 6.80 (d, 1H), 6.82-6.83 (m, 1H), 7.10 (d, 1H), 7.27-7.38 (m, 5H), 7.42 (d, 1H), 7.57 (d, 1H).

Example 5

1-{5-[(Cyclopropylmethyl)(methyl)amino]-3-{[3-methoxy-4-(4-methyl-1H-imidazol-1-yl)-phenyl]amino}-1H-1,2,4-triazol-1-yl}-2-methylpropan-2-ol

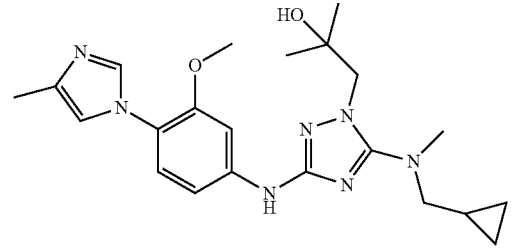 [SMILES: COc1cc(Nc2nc(N(C)CC3CC3)n(CC(C)(C)O)n2)ccc1-n1cnc(C)c1]

1-{3-Bromo-5-[(cyclopropylmethyl)(methyl)amino]-1H-1,2,4-triazol-1-yl}-2-methylpropan-2-ol (197 mg, 0.65 mmol) was dissolved in dioxane (5 mL) and dimethylacetamide (0.2 mL) in a pressure-resistant tube. 3-Methoxy-4-(4-methyl-1H-imidazol-1-yl)aniline dihydrochloride (180 mg, 0.65 mmol), cesium carbonate (847 mg, 2.6 mmol) and Xantphos (64 mg, 0.17 mmol) were added. The reaction mixture was degassed with $N_2$ for 10 minutes. Pd(OAc)$_2$ (29 mg, 0.13 mmol) was added and the tube was purged with $N_2$, sealed and heated to 120° C. for 16 h. The mixture was diluted with EtOAc (100 mL). The mixture was washed with water (3×10 mL) and brine (10 mL), dried over magnesium sulfate, and concentrated. The residue was purified on a silica gel cartridge eluting with gradients of MeOH in DCM. The residue triturated with MeCN to give the title compound as a solid (147 mg, 53%).

MS (ESI) m/z 426 [M+H]$^+$. $^1$H NMR (400 MHz, CDCl$_3$): ppm 0.14-0.19 (m, 2H), 0.52-0.58 (m, 2H), 0.94-1.05 (m, 1H), 1.20 (s, 6H), 2.29 (s, 3H), 2.92 (s, 3H), 2.98 (d, 2H), 3.83 (s, 3H), 3.91 (s, 2H), 4.73 (s, 1H), 6.57 (s, 1H), 6.75 (dd, 1H), 6.84 (s, 1H), 7.11 (d, 1H), 7.41 (d, 1H), 7.58 (s, 1H).

Example 6

1-[5-(Benzylamino)-3-{[3-methoxy-4-(4-methyl-1H-imidazol-1-yl)phenyl]amino}1H-1,2,4-triazol-1-yl]-2-methylpropan-2-ol

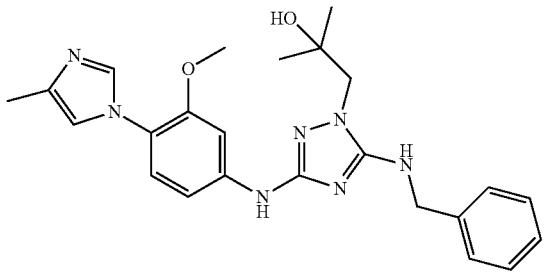 [SMILES: COc1cc(Nc2nc(NCc3ccccc3)n(CC(C)(C)O)n2)ccc1-n1cnc(C)c1]

1-[5-(Benzylamino)-3-bromo-1H-1,2,4-triazol-1-yl]-2-methylpropan-2-ol (200 mg, 0.62 mmol), 3-methoxy-4-(4-methyl-1H-imidazol-1-yl)aniline dihydrochloride (170 mg, 0.62 mmol), cesium carbonate (808 mg, 2.48 mmol), Xantphos (72 mg, 0.12 mmol) and Pd(OAc)$_2$ (29 mg, 0.12 mmol) were mixed in dioxane (3 mL) and N,N-dimethylacetamide (0.1 mL). The reaction mixture was purged under nitrogen for 10 minutes. The reaction mixture was heated to 120° C. overnight. The residue was filtered through diatomaceous earth, washed with methanol and concentrated in vacuo. The residue was purified on a silica gel cartridge using gradients of MeOH in CH$_2$Cl$_2$ as eluent. The residue was purified on a 25 g C18 cartridge using gradients of MeOH in water to give the title compound as a solid (120 mg, 43%).

MS (ESI) m/z 448 [M+H]$^+$. $^1$H NMR (400 MHz, CDCl$_3$): ppm 1.32 (s, 6H), 2.28 (s, 3H), 3.78 (s, 3H), 3.79 (s, 2H), 4.55 (d, 1H), 5.30 (t, 1H), 6.51 (s, 1H), 6.80 (dd, 1H), 6.83 (s, 1H), 7.08 (d, 1H), 7.28-7.37 (m, 5H), 7.44 (d, 1H), 7.55 (d, 1H).

Example 7

1-{5-[Benzyl(methyl)amino]-3-{[3-methoxy-4-(4-methyl-1H-imidazol-1-yl)phenyl]amino}-1H-1,2,4-triazol-1-yl}-2-methylpropan-2-ol

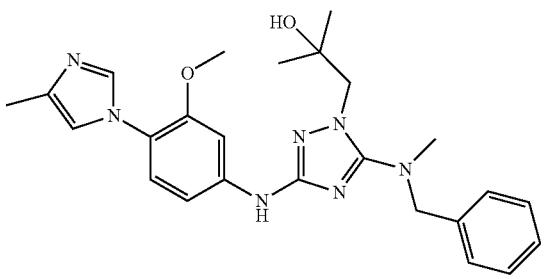 [SMILES: COc1cc(Nc2nc(N(C)Cc3ccccc3)n(CC(C)(C)O)n2)ccc1-n1cnc(C)c1]

1-{5-[Benzyl(methyl)amino]-3-bromo-1H-1,2,4-triazol-1-yl}-2-methylpropan-2-ol (250 mg, 0.74 mmol), 3-methoxy-4-(4-methyl-1H-imidazol-1-yl)aniline dihydrochloride (204 mg, 0.74 mmol), cesium carbonate (964 mg, 2.96 mmol), Xantphos (87 mg, 0.15 mmol) and Pd(OAc)$_2$ (33 mg, 0.15 mmol) were mixed in dioxane (3 mL) and N,N-dimethylacetamide (0.1 mL). The reaction mixture was purged under nitrogen for 10 minutes. The reaction mixture was heated at 120° C. overnight in a sealed vessel. The residue was filtered through diatomaceous earth, washed with methanol and concentrated in vacuo. The crude product was purified on a silica gel cartridge using gradients of MeOH in DCM as eluent. The residue was triturated with MeCN to give the title compound as a solid (80 mg, 23%).

MS (ESI) m/z 462 [M+H]$^+$. $^1$H NMR (400 MHz, CDCl$_3$): ppm 1.17 (s, 6H), 2.29 (s, 3H), 2.83 (s, 3H), 3.83 (s, 3H), 3.87 (s, 2H), 4.33 (s, 2H), 4.67 (s, 1H), 6.58 (s, 1H), 6.76 (dd, 2.2 Hz, 1H), 6.84 (s, 1H), 7.12 (d, 1H), 7.29-7.41 (m, 5H), 7.59 (s, 1H).

Biological Assays

The level of activity of the compounds on Aβ formation was tested using the following methods:

HEK Assay

Compounds were diluted in 100% DMSO and stored at 20° C. prior to use. Human Embryonic Kidney (HEK) cell line stably expressing APP with the Swedish mutation (APPswe) was cultured using Dulbecco's Modified Eagles medium (DMEM) supplied with 4500 g/L glucose, Na-pyruvate and GlutaMAX, 10% Foetal bovine serum, 100 U/mL penicillin-streptomycin (PEST), 1× non-essential amino acids (NEAA), 10 μM Hepes, 100 μg/mL Zeocine. Cells at about 80% confluence were washed with PBS, detached from culture flasks using 1×Trypsin/EDTA diluted in PBS, re-suspended in cell media and plated in 384-well poly-d-lysine coated cell culture plates at about 10000-15000 cells/well, in 25 μL cell media. Optionally, cryopreserved cells (frozen and stored at −140° C. in 90% cell media and 10% DMSO) were thawed, washed and plated as above. Next the cells were incubated for 15-24 h at 37° C. and 5% CO$_2$, after which cell medium was changed. Fresh medium containing test compound diluted ×200 from prepared compound plate was added to the cells before further incubation for 4-6 hours at 37° C. and 5% CO$_2$. After incubation with test compound the amount of Aβ peptides, including Aβ42, Aβ40, Aβ39, Aβ38 and Aβ37, secreted to cell medium was analyzed using the electrochemiluminescence assay technology from Meso Scale Discovery Technology, in combination with specific antibodies raised against the different Aβ peptides. Potential cytotoxic effects of the compounds were assayed by measuring the ATP content (ViaLight) from cell lysate.

PCN Assay

Compounds were diluted in 100% DMSO and stored at 20° C. prior to use. Primary cortical neuronal cells (PCN) were isolated from 16-day mouse embryos and cultured in Ham's F12 media containing 10% Foetal bovine serum, 10 mM Hepes, 2 mM L-glutamine and 100 U/ml Penicillin-Streptomycin. 150000-250000 cells/well, in 200 µl cell media were seeded onto 96-well poly-D-Lysine coated plates. After incubation at 37° C., 5% $CO_2$ for five days, the media was exchanged for fresh medium containing test compound diluted ×100, before further incubation for 16-20 hours at 37° C. and 5% $CO_2$. After incubation with test compound the amount of Aβ42 peptides secreted to cell medium was analyzed using the solid phase sandwich Enzyme-Linked-Immuno-Sorbent Assay (ELISA)-kit from Invitrogen for detection of mouse βAmyloid 1-42. Potential cytotoxic effects of the compounds were assayed by measuring the ATP content (Via Light) from cell lysate.

Results

Biological data on exemplified compounds are given below in Table 1.

TABLE 1 pIC$_{50}$ values in the HEK and PCN assays for the examples of the present invention.

| Example number | pIC50 Aβ42 HEK assay | pIC50 Aβ42 PCN assay |
|---|---|---|
| 1 | 7.1 | 6.8 |
| 2 | 7.2 | ND |
| 3 | 7.2 | ND |
| 4 | 7.0 | ND |
| 5 | 7.1 | ND |
| 6 | 7.7 | 7.8 |
| 7 | 7.8 | 7.7 |

ND = not determined

The total IC50 Aβ and the ratio of Aβ 42/40 was improved.

The invention claimed is:

1. A compound of formula (I)

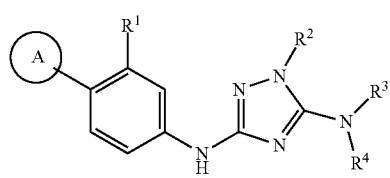

(I)

wherein:
A is 4-methyl-1H-imidazol-1-yl;
$R^1$ is methoxy;
$R^2$ is $C_{1-4}$alkyl optionally substituted with one substituent selected from the group consisting of hydroxy, halo, and cyano, or $R^2$ is phenyl-$C_{1-3}$-alkyl, wherein the phenyl is optionally substituted with one or more fluoro; and
$R^3$ and $R^4$ are each independently selected from the group consisting of hydrogen, $C_{1-3}$-alkyl, hydroxy-$C_{1-4}$-alkyl, $C_{3-7}$-cycloalkyl-$C_{1-3}$-alkyl, and phenyl-$C_{1-2}$-alkyl;
or a pharmaceutically acceptable salt thereof.

2. The compound according to claim 1, or a pharmaceutically acceptable salt thereof, wherein $R^2$ is hydroxy-$C_{1-4}$-alkyl.

3. The compound according to claim 1, or a pharmaceutically acceptable salt thereof, wherein $R^2$ is phenyl-$C_{1-2}$-alkyl.

4. The compound according to claim 1, or a pharmaceutically acceptable salt thereof, having formula (Ia)

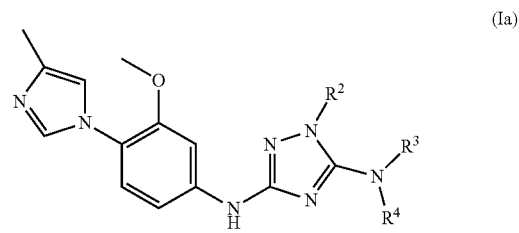

(Ia)

wherein:
$R^2$ is $C_{1-4}$-alkyl, which is optionally substituted with one hydroxy substituent, or is phenyl-$C_{1-2}$-alkyl;
$R^3$ is hydroxy-$C_{1-6}$-alkyl, $C_{3-7}$-cycloalkyl-$C_{1-3}$-alkyl, or phenyl-$C_{1-3}$-alkyl; and
$R^4$ is hydrogen, $C_{1-3}$-alkyl or $C_{3-7}$-cycloalkyl-$C_{1-3}$-alkyl.

5. The compound according to claim 4, or a pharmaceutically acceptable salt thereof, wherein $R^2$ is hydroxy-$C_{1-4}$-alkyl.

6. The compound according to claim 4, or a pharmaceutically acceptable salt thereof, wherein $R^2$ is benzyl.

7. The compound according to claim 1, selected from the group consisting of:
1-[(1-Benzyl-3-{[3-methoxy-4-(4-methyl-1H-imidazol-1-yl)phenyl]amino}-1H-1,2,4-triazol-5-yl)(methyl)amino]-2-methylpropan-2-ol;
1-{5-[(Cyclopropylmethyl)(methyl)amino]-3-{[3-methoxy-4-(4-methyl-1H-imidazol-1-yl)phenyl]amino}-1H-1,2,4-triazol-1-yl}-2-methylpropan-2-ol;
1-[5-(Benzylamino)-3-{[3-methoxy-4-(4-methyl-1H-imidazol-1-yl)phenyl]amino}1H-1,2,4-triazol-1-yl]-2-methylpropan-2-ol; and
1-{5-[Benzyl(methyl)amino]-3-{[3-methoxy-4-(4-methyl-1H-imidazol-1-yl)phenyl]amino}-1H-1,2,4-triazol-1-yl}-2-methylpropan-2-ol;
or a pharmaceutically acceptable salt of any foregoing compound.

8. The compound according to claim 1, selected from the group consisting of:
$N^5$-(Cyclopropylmethyl)-$N^3$-[3-methoxy-4-(4-methyl-1H-imidazol-1-yl)phenyl]-1-methyl-1H-1,2,4-triazole-3,5-diamine;
5-N,5-N-Bis(cyclopropylmethyl)-3-N-[3-methoxy-4-(4-methyl-1H-imidazol-1-yl)phenyl]-1-methyl-1H-1,2,4-triazole-3,5-diamine; and
5-N-(Cyclopropylmethyl)-3-N-[3-methoxy-4-(4-methyl-1H-imidazol-1-yl)phenyl]-1-(2-methylpropyl)-1H-1,2,4-triazole-3,5-diamine;
or a pharmaceutically acceptable salt thereof.

9. A pharmaceutical composition comprising as active ingredient a therapeutically effective amount of a compound according to claim 1, or a pharmaceutically acceptable salt thereof, in association with a pharmaceutically acceptable excipient, carrier or diluent.

10. A pharmaceutical composition comprising
(i) a compound of formula (I) according to claim 1, or a pharmaceutically acceptable salt thereof, (ii) an additional therapeutic agent, or a pharmaceutically acceptable salt thereof, and (iii) a pharmaceutically acceptable excipient, carrier or diluent.

11. The pharmaceutical composition according to claim 10, wherein the additional therapeutic agent is selected from the group consisting of acetyl cholinesterase inhibitors, anti-inflammatory agents, cognitive enhancing agents, memory enhancing agents, and atypical antipsychotic agents.

12. A pharmaceutical composition comprising
(i) a compound of formula (Ia) according to claim 4, or a pharmaceutically acceptable salt thereof,
(ii) at least one agent selected from the group consisting of onepezil, galantamine, rivastigmine, tacrine and memantine, Olanzapine, Aripiprazole, Risperidone, Quetiapine, Clozapine, Ziprasidone and Olanzapine/Fluoxetine, and
(iii) a pharmaceutically acceptable excipient, carrier or diluent.

13. A method of treating an Aβ-related pathology in a patient in need thereof, wherein the Aβ-related pathology is selected from the group consisting of β-amyloid angiopathy, Alzheimer's disease, attention deficit symptoms associated with Alzheimer's disease, and neurodegeneration associated with Alzheimer's disease, comprising administering to the patient a therapeutically effective amount of a compound according to claim 1, or a pharmaceutically acceptable salt thereof.

14. The method according to claim 13, wherein the Aβ-related pathology is Alzheimer's disease.

15. The method of claim 13, further comprising administering to the patient at least one acetyl cholinesterase inhibitor, anti-inflammatory agent, cognitive enhancing agent, memory enhancing agent, or atypical antipsychotic agent.

16. A method of treating an Aβ-related pathology in a patient in need thereof, wherein the Aβ-related pathology is selected from the group consisting of β-amyloid angiopathy, Alzheimer's disease, attention deficit symptoms associated with Alzheimer's disease, and neurodegeneration associated with Alzheimer's disease, comprising administering to the patient a therapeutically effective amount of a pharmaceutical composition comprising (i) a compound of formula (Ia) according to claim 8, or a pharmaceutically acceptable salt thereof, and (ii) at least one agent selected from the group consisting of onepezil, galantamine, rivastigmine, tacrine and memantine, Olanzapine, Aripiprazole, Risperidone, Quetiapine, Clozapine, Ziprasidone and Olanzapine/Fluoxetine.

17. The method according to claim 15, wherein the Aβ-related pathology is Alzheimer's disease.

18. The method according to claim 16, wherein the Aβ-related pathology is Alzheimer's disease.

* * * * *